(12) United States Patent
Scharf

(10) Patent No.: US 6,947,780 B2
(45) Date of Patent: Sep. 20, 2005

(54) AUDITORY ALARMS FOR PHYSIOLOGICAL DATA MONITORING

(75) Inventor: Tom D. Scharf, Palm Harbor, FL (US)

(73) Assignee: Dolphin Medical, Inc., Hawthorne, CA (US)

( * ) Notice: Subject to any disclaimer, the term of this patent is extended or adjusted under 35 U.S.C. 154(b) by 226 days.

(21) Appl. No.: 10/403,858

(22) Filed: Mar. 31, 2003

(65) Prior Publication Data

US 2004/0193026 A1 Sep. 30, 2004

(51) Int. Cl.[7] .............................................. A61B 5/00
(52) U.S. Cl. ...................... 600/323; 600/300; 600/481
(58) Field of Search ................................. 600/300, 310, 600/322–324, 453, 481, 485, 500, 504, 508, 514, 529; 128/920; 340/373.1

(56) References Cited

U.S. PATENT DOCUMENTS

| | | | | |
|---|---|---|---|---|
| 3,658,060 A | * | 4/1972 | Eklof | 600/486 |
| 4,653,498 A | * | 3/1987 | New et al. | 600/324 |
| 4,727,570 A | | 2/1988 | Tarbouriech | |
| 4,933,980 A | | 6/1990 | Thompson | |
| 5,730,140 A | | 3/1998 | Fitch | |
| 5,802,187 A | | 9/1998 | Hsu | |
| 6,449,501 B1 | * | 9/2002 | Reuss | 600/323 |
| 6,542,764 B1 | * | 4/2003 | Al-Ali et al. | 600/323 |
| 2004/0243016 A1 | * | 12/2004 | Sanderson et al. | 600/532 |

* cited by examiner

Primary Examiner—Eric F. Winakur
(74) Attorney, Agent, or Firm—Patent Metrix

(57) ABSTRACT

The present invention provides methods and devices for monitoring physiological data such that a health care provider is able to effectively monitor a patient's health status, including, for example, blood flow characteristics, without having to maintain constant visual contact. In one embodiment of the present invention, a physiological data monitoring system measures at least one physiological characteristic wherein the physiological data monitoring system comprises a sensor unit and a monitoring unit in data communication with the sensor unit. The monitoring unit has a sonification module that comprises one programmable sound generator module to produce a plurality of signals indicative of a physiological parameter and a memory module for storing a plurality of control parameters for managing the programmable sound generator module, wherein the plurality of signals produced have a plurality of frequencies modified in accordance with at least one physiological data value. More specifically, the present invention provides a pulse oximetry sonification system that generates fixed frequency singular and/or combined amplitude-adjusted dual audio tones corresponding to predetermined transition and/or intermediate points over a range of $SpO_2$ measurements.

9 Claims, 4 Drawing Sheets

| SpO2 Level | 100% | 97% | 94% | 91%. |
|---|---|---|---|---|
| Frequency Value | 661 Hz | 645 Hz | 620 Hz | 600 Hz |

Figure 3

AUDITORY ALARMS FOR PHYSIOLOGICAL DATA MONITORING

FIELD OF THE INVENTION

The invention relates generally to physiological monitoring systems, and more specifically, to systems and methods that operate with physiological monitoring systems to generate audible indicators of a detected physiological condition.

BACKGROUND OF THE INVENTION

In certain applications, a user may need to monitor the status of an activity, function, variable, or other data by relying on auditory, as opposed to visual, indicators. For example, in many situations requiring physiological monitoring, such as in the course of surgery, providing anesthesia, or tracking critical vital signs, a user needs to visually focus on tasks other than monitoring and, therefore, is unable to visually monitor the physiological data for important changes or variations. In such cases, the monitoring of physiological data may best be achieved through the sonification of physiological data. Sonifying data generates auditory indicators by expressing received information as humanly perceptible sound patterns.

An exemplary physiological data monitoring device is a pulse oximeter. Pulse oximeters are used to monitor and report on blood flow characteristics including, but not limited to, the level of arterial blood saturation, the volume of individual blood pulsation supplying a tissue, and the rate of blood pulsation corresponding to each heartbeat. Where important changes or variations occur in blood flow characteristics, it would be valuable to indicate such changes or variations using auditory indicators such that health care providers, including doctors, nurses, technicians, and other persons, can be warned of a patient's health status without having to constantly visually monitor the pulse oximeter.

Oximeters typically comprise monitoring units that incorporate modules for generating audible alarm signals when a particular physiological parameter varies beyond certain safe limits. These oximeters use well-defined audio signaling techniques for the limited purpose of conveying alarm situations. For example, an existing oximeter generates a tonal signal that has a pitch proportional to the ratio of oxygen saturation and a sequential repetition proportional to pulse.

However, a continuous variation of audio pitch with the level of oxygen saturation ($SpO_2$) does not allow a user to effectively associate a particular tone with a certain $SpO_2$ reading. Also, prior art oximeters use special-purpose monitor units that incorporate audio generation circuitry, often implemented in hardware, that offer limited scope for manipulation of various acoustic variables governing an audio signal.

Therefore, an approach to physiological data monitoring is needed whereby audio signals are generated that represent predetermined transition points over a range of physiological data measurements, such as a range of $SpO_2$ measurements. It is further needed to implement a sonification system in software such that the alarm signals can be programmed or manipulated by a user and such that the sonification system can be used on any general-purpose computing device such as a PC, PDA or a laptop computer.

SUMMARY OF THE INVENTION

In one embodiment of the present invention, a physiological data monitoring system measures at least one physiological characteristic wherein the physiological data monitoring system comprises a sensor unit and a monitoring unit in data communication with the sensor unit. The monitoring unit has a sonification module that comprises at least one programmable sound generator module to produce a plurality of signals indicative of a physiological parameter and a memory module for storing a plurality of control parameters for managing the programmable sound generator module, wherein the plurality of signals produced have a plurality of frequencies modified in accordance with at least one physiological data value.

Optionally, the monitoring unit is implemented in a general purpose computing platform selected from at least one a personal computer or a portable computing device such as a personal data assistant. Further optionally, the programmable sound generator module comprises a tone generator control that generates tonal signals of a plurality of frequencies by modifying a reference frequency signal generated by an oscillator, an amplitude control for modifying amplitudes of the tonal signals, and a mixer to combine the plurality of tonal signals that have been suitably amplitude adjusted.

Preferably, in the one embodiment, the sonification module generates frequency tones, at a plurality of predetermined transition points, corresponding to a measured physiological parameter. In another embodiment, that parameter is pulse rate and/or $SpO_2$ level. In yet another embodiment, the transition points represent an appreciable change in the measured physiological parameter where the appreciable change has a value that is programmable by a user.

The present invention is also directed toward a pulse oximeter monitoring unit for measuring at least one blood flow characteristic through the application of at least one sensor having a plurality of light sources and at least one photodetector. One embodiment of the monitoring unit comprises a processor in data communication with the sensor wherein the processor transmits control signals to the light sources, a data acquisition module in data communication with the processor and the sensor unit wherein the data acquisition module receives input signals from the photodetectors, a memory module in data communication with the data acquisition module, and a sonification module in data communication with the memory module wherein the sonification module generates frequency tones, at a plurality of predetermined transition points, corresponding to a measured $SpO_2$ level. The transition points represent an appreciable change in the measured $SpO_2$ level and, in one embodiment, are programmable by a user and in another embodiment may be established as a change in the range of 3%, 2% to 5%, 1% to 10% or less than 15%.

Optionally, the monitoring unit is implemented in a general purpose computing platform selected from at least one a personal computer or a portable computing device such as a personal data assistant, and the sonification module comprises at least one programmable sound generator module to produce a plurality of signals indicative of the measured $SpO_2$ level and a memory module for storing a plurality of control parameters for managing the programmable sound generator module.

Further optionally, the programmable sound generator module comprises a tone generator control that generates tonal signals of a plurality of frequencies by modifying a reference frequency signal generated by an oscillator, and an amplitude control for modifying amplitudes of the tonal signals.

The present invention is further directed towards a method of monitoring a patient's physiological status using a monitoring system that measures at least one physiological characteristic. One embodiment of the method comprises the steps of sensing a value for a physiological characteristic, transmitting the value to a sonification module, receiving in the sonification module the transmitted value, comparing the value to a plurality of predetermined transition points, if the value matches one of said transition points, selecting a corresponding stored frequency value, based on the frequency value selected, generating signal waveforms having a frequency corresponding to the stored frequency value, transmitting the waveforms to a digital to analog converter, amplifying the converted waveforms, and transforming the amplified converted waveforms to acoustic energy.

Optionally, the physiological characteristic being measured is at least one of pulse rate or $SpO_2$ level. Further optionally, the method includes, if the value does not match one of the transition points, identifying at least two transition points that approximate the value and selecting at least two frequency values corresponding to the at least two transition points.

Accordingly, it is an object of the present invention to provide a pulse oximetry sonification system that generates fixed frequency singular audio tones corresponding to predetermined transition points over a range of $SpO_2$ measurements.

It is another object of the present invention to generate dual audio tone signals for intermediate $SpO_2$ measurements falling between a set of transition points closest to the measured value.

It is yet another object of the present invention to shape the audio tone signals by mixing them with the plethysmographic signals for a user's improved association of the audible indication with changes in the measured levels of $SpO_2$ and also enabling the user to hear the systolic and diastolic shape that is typical of oximetry signals.

It is yet another object of the present invention to generate audible signals that are pleasant to hear.

It is yet another object of the present invention to implement the sonification system in software such that the frequencies of the singular audio tones as well as the modification of the amplitudes of the dual audio tones can be programmed or manipulated by a user.

It is still another object of the present invention to implement the sonification system software on any general-purpose computing device such as a PC, PDA or a laptop computer so that the sonification system can harness the processing, storage and other utilities that are typically available built-in with such computing devices.

BRIEF DESCRIPTION OF THE DRAWINGS

These and other features and advantages of the present invention will be appreciated, as they become better understood by reference to the following Detailed Description when considered in connection with the accompanying drawings, wherein:

FIG. 3 is an embodiment of a memory table that stores a set of frequency values for a plurality of exemplary transition points.

DETAILED DESCRIPTION OF THE INVENTION

The present invention provides methods and devices for monitoring physiological data such that a health care provider is able to effectively monitor a patient's health status, including, for example, blood flow characteristics, without having to maintain constant visual contact. The present invention will be described with reference to aforementioned drawings. One of ordinary skill in the art would appreciate that the applications described herein are examples of how the broader concept can be applied. Specifically, while the present invention will be described in relation to a pulse oximeter, one of ordinary skill in the art would appreciate that the auditory signaling system disclosed herein could be used with any type of physiological monitoring device, including, but not limited to, EKGs.

Pulse oximetry involves measurement of the effect arterial blood has on the intensity of light reflected from or transmitted through tissue. More particularly, the volume of blood in the tissue is a function of the arterial pulse, with a greater volume present at systole and a lesser volume present at diastole. Because blood absorbs some of the light passing through the tissue, the intensity of the light emerging from the tissue is inversely proportional to the volume of blood in the tissue.

Thus, the emergent light will vary with the arterial pulse and can be used to indicate a subject's pulse rate. In addition, the absorption coefficient of oxy-hemoglobin is different from that of deoxygenated hemoglobin for most wavelengths of light. Therefore, differences in the amount of light absorbed by the blood at two different wavelengths can be used to indicate the hemoglobin oxygen saturation. Thus, measurement of the amount of light transmitted through or reflected from, for example, tissue, such as a finger, can be used to determine both the subject's pulse rate and hemoglobin oxygen saturation.

Figure 1:
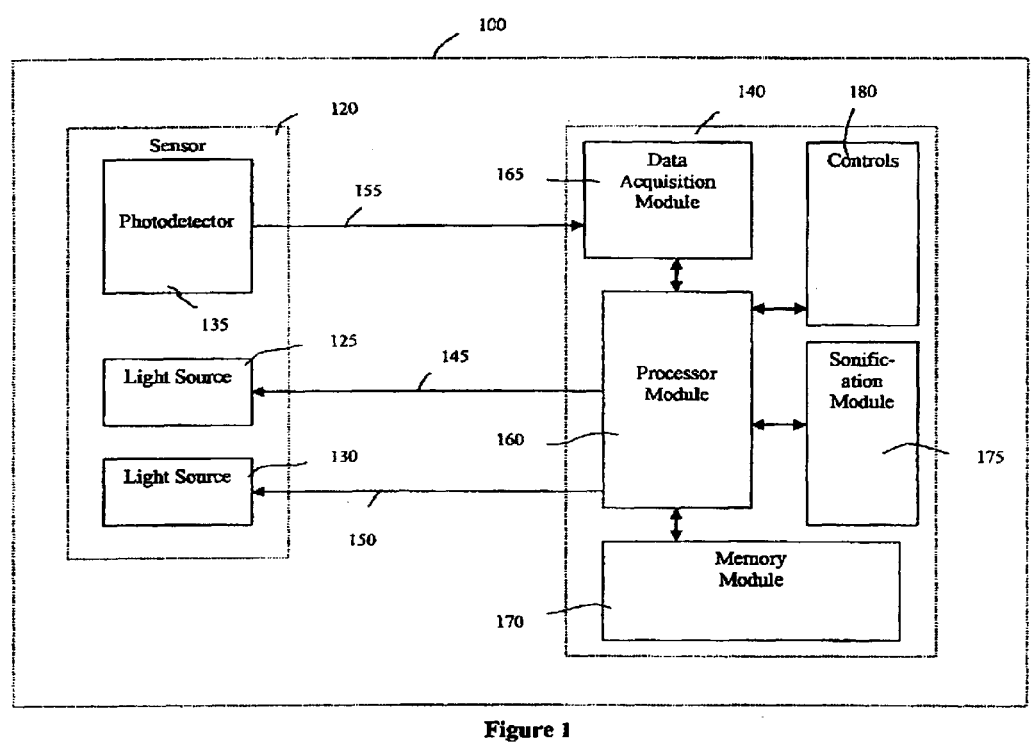
FIG. 1 is a functional block diagram of an exemplary pulse oximetry system.

FIG. 1 shows an embodiment of a pulse oximeter 100 comprising a sensor 120 for application to a tissue site (either human or non-human), in communication with a monitor unit 140 using electrical wiring or through wireless coupling. The sensor 120 contains light sources 125 and 130, typically light-emitting diodes (LEDs) controlled by the monitor 140, and photodetector(s) 135 returning signal(s) 155 to the monitor 140. The monitor unit 140 transmits control signals, 145 and 150, to the sensor 120 and receives input signals 155 back.

In the present embodiment, the control signals, 145 and 150, are directed from the processor module 160 to the red 125 and infrared 130 LEDs while the signal(s) 155 from the photodetector(s) 135 are directed to the data acquisition module 165. The monitor unit 140 comprises data acquisition module 165, processing module 160, memory module 170, sonification module 175, and visual display plus keypad or other operator controls 180 known to persons of ordinary skill in the art.

During operation, the data acquisition module 165 digitizes the analog signal 155 for use by the processing module 160. The processing module 160 drives the light sources 125 and 130; processes received signals 155 from the detector 135 to calculate blood oxygenation, pulse rate or any other physiological parameter known in the art and audibly presents the physiological parameter to a user through the sonification module 175.

Variations of this design would be known to those of ordinary skill in the art, such as variations relating to the location, number and nature (frequencies) of the light source(s), transfer of the signals between sensor and monitor, intended use of the sensor at different tissue sites, features of the monitor unit including variations in signal processing techniques, packaging of the sensor or monitor components, processing in embedded versus general-purpose computing devices, and distribution of components over a network. These variations do not change the fundamental principle of pulse oximetry and the intent of the present invention.

For example, in an alternative embodiment, the sensor module 120 may output a digitized signal to the monitoring module 140. Such a sensor module may comprise a plurality of light emitting diodes (LEDs), a photodiode, current to voltage converter, a plurality of filters, amplifier, sample and hold circuit, analog to digital converter, and a transceiver that may communicate via cable or wirelessly with a monitoring unit. The LEDs illuminate a volume of intravascular blood in vivo by emitting electromagnetic radiation through a body part at a constant intensity. The electromagnetic radiation is transmitted/reflected by the intravascular blood as an optical signal with a time varying intensity, which is detected by the photodiode. The photodiode generates a low-level current proportional to the intensity of the received electromagnetic radiation. The current is converted to a voltage by a current to voltage converter, which is an operational amplifier in a current to voltage (transimpedance) configuration. The signal is then filtered with a filter to remove unwanted frequency components, amplified with the amplifier, sampled by a sample and hold circuit, and subsequently digitized with a high-resolution analog to digital converter.

It is preferred that a digital oximeter system be used in the present invention. Analog oximeters convert sensor output signals into analog voltage by employing a plurality of analog circuits to further filter, amplify and sample these signals. As known to persons of ordinary skill in the art, analog oximeters suffer from disadvantages such as the need to carefully match the analog components to minimize errors which can result from differences in gain or frequency response in the analog circuits and the inability to detect low level signals such as those obtained from monitoring fetal conditions. Therefore, it is desirable to use a digital oximeter system, which converts the current signals from the photodetector(s) directly to digital voltage values, using a charge digitizing analog to digital converter, without first converting to analog voltages. Despite cited disadvantages, a traditional analog oximeter has been described so that persons of ordinary skill in the art would appreciate that the present invention encompasses the use of both an analog and a digital oximeter and that either oximeter system can be used to practice the present invention.

Referring back to FIG. 1, during operation, the pulsatile oximetry signals 155 sensed by the photodetector(s) 135 may be digitized by the data acquisition module 165 and stored in memory module 170 that may comprise suitable signal storage means such as circular (ring) buffers, RAM, EPROM, flash memory or any other electronic storage known in the art. These digitized signal data may further undergo a plurality of signal conditioning processes such as removal of ambient light bias, line frequency noise rejection, band pass filtering and signal amplification intended to remove noise. Similarly, the plethysmographic pulsatile content of the oximetry signal may be emphasized using typical adaptive peak-valley search of the signal data to distinguish possible systolic and diastolic phases. Finally, the conditioned signals may be processed by the processing module using a plurality of oximetry methods and techniques known to persons of ordinary skill in the art.

In accordance with a preferred embodiment, the monitor unit 140 comprises electronic microprocessor based devices such as a general purpose personal computer or portable devices such as laptop computers, personal digital assistants (PDAs), electronic books, handheld computers or any other portable or non-portable computing device known to persons of ordinary skill in the art. Thus, the data acquisition and memory modules, 165 and 170 respectively, are standard hardware implementations available packaged with a conventional PDA or computing device, with the processing/conditioning and sonification modules, 160 and 175 respectively, being implemented as a plurality of software applications. The processing module 160 calculates and provides readings on pulse rate and the level of oxygen saturation in arterial blood ($SpO_2$) to the sonification module 175 that generates intermittent audible signals synchronized with the detected pulse rate and that vary with the level of oxygen saturation in arterial blood ($SpO_2$).

Figure 2:
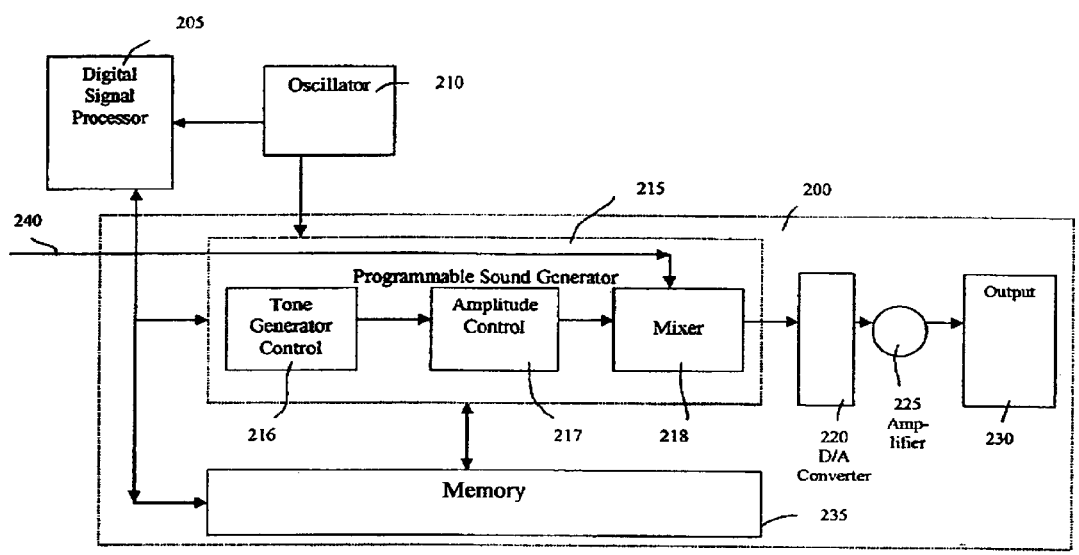
FIG. 2 is a functional block diagram of one embodiment of a sonification system.

FIG. 2 shows a functional block diagram of a preferred embodiment of a sonification system 200 that is implemented by means of suitable software in a digital signal processor 205 that may be comprised of a microprocessor or a microcomputer having a central processing unit. The system 200 comprises at least one programmable sound generator (PSG) module 215 to produce a plurality of digital audio tone signals indicative of a physiological parameter, such as, the level of oxygen saturation in arterial blood, and a memory module 220 for storing a plurality of control parameters for managing the PSG system 215. The memory module 220 comprises suitable electronic storage means such as circular (ring) buffers, RAM, EPROM, EEPROM, flash memory or any other electronic storage known in the art. Although, in FIG. 2, the memory module 220 has been shown as a separate additional module of the sonification system 200, it should be evident to persons of ordinary skill in the art that the module 220 can alternatively or additionally be implemented in the standard storage hardware available packaged with conventional portable and non-portable computing devices that function as the monitor unit 140 of FIG. 1. Thus, for example, the sonification system 200 when implemented as a software package on a general-purpose portable or non-portable computing device, communicates with the standard memory implementations available packaged with the computing device. The PSG module 215 further comprises a tone generator control 216 that generates tonal signals of a plurality of frequencies by suitably modifying the basic reference frequency signals generated by a digital oscillator 210 such as a TTL clock, an amplitude control 217 for modifying amplitudes of the tonal signals and a mixer 218 to combine the plurality of tonal signals that have been suitably amplitude adjusted. The output of the PSG module 215 is supplied via a digital to analog converter 220 and via an audio amplifier 225 to a sound output device 230, such as a headphone, a speaker or any other acoustic energy outputting system known in the art.

In a preferred embodiment, the sonification system 200 is programmed to generate fixed frequency tones corresponding to measured $SpO_2$ levels at a plurality of predetermined transition points along an entire range of measured oxygen saturation values. These transition points represent a suitable change in the value of the measured $SpO_2$ levels.

For example, if the measurable range of $SpO_2$ for the oximeter varies from a level of 100% to a level of 80% then the plurality of transition points would be identifiable at every x% change in the measured level of $SpO_2$, wherein the variable x is preferably selectable by a user. In a preferred embodiment the transition points occur at every 3% change in the level of measured $SpO_2$. Therefore, at every 3% change in the level of measured $SpO_2$ a corresponding tone of a suitable fixed frequency $f_x$ is generated synchronized with the pulse rate wherein the tonal frequency $f_x$ is different for different transition points.

For example, if the $SpO_2$ level is 100% then a 661 Hertz (Hz) tone is sounded synchronized with the pulse rate. If the $SpO_2$ level decreases by 3% to the next transition point of 97% then a different frequency tone of approximately 645 Hz is sounded. If the measured $SpO_2$ level decreases to 94% than an approximately 620 Hz tone is generated. The process continues on for each increment of percentage-based decrease. The tonal frequencies corresponding to the transition points are chosen from within the range of frequencies audible to the human ear and, preferably, such that a user can not only easily discern the difference in the tonal frequencies at different transition points but also associate the change in the tone with a positive or negative variation in the underlying $SpO_2$ level measured. Further, one of ordinary skill in the art would appreciate that, while the present example disclosed a decreasing $SpO_2$ level scenario, it would similarly apply to situations of increasing $SpO_2$ level and would further similarly apply to situations of increasing or decreasing levels for other physiological data being monitored.

Referring to FIG. 2, the tone generator control 216 divides the basic frequency pulse of the clock 210 to generate a signal waveform of a desired frequency $f_x$ that corresponds to the measured oxygen saturation level matching one of a range of predetermined transition points. The memory module 220 stores a plurality of frequency values, corresponding to each transition point, that are used as input by the tone generator control 216 to adjust the clock frequency suitably. FIG. 3 shows an exemplary memory table that stores a set of frequency values for each transition point occurring at every 3% $SpO_2$ level change. It should, however, be appreciated by persons of ordinary skill in the art that the table of FIG. 3 is only exemplary and that it can be suitably modified, in alternative embodiments, to have additional or fewer transition points and therefore associated frequency values.

In addition to sounding different frequency tones at the transition points, audible indications are also generated for intermediate $SpO_2$ levels that fall within any two consecutive transition points. In accordance with a preferred embodiment, a dual tone is sounded for intermediate $SpO_2$ levels, measured at y% intervals between the transition points, wherein the variable y is preferably selectable by a user, by suitably adjusting the amplitudes of the two frequency tones closest to the intermediate $SpO_2$ level and combining the two amplitude adjusted frequency tones.

In a preferred embodiment, the dual tone indications are generated for intermediate $SpO_2$ levels measured at 1% intervals between the transition points occurring at 3% values. Referring back to FIG. 2, for $SpO_2$ levels falling between any two bounding transition points, the tone generator control 216 produces two signal waveforms of frequencies $f_{x1}$ and $f_{x2}$ that correspond to the two bounding transition points. The two frequency signals are then suitably adjusted by the amplitude control 217 and passed through the mixer 218 where the two amplitude adjusted signals of frequencies $f_{x1}$ and $f_{x2}$ are combined to produce a dual tone signal.

Figure 4:
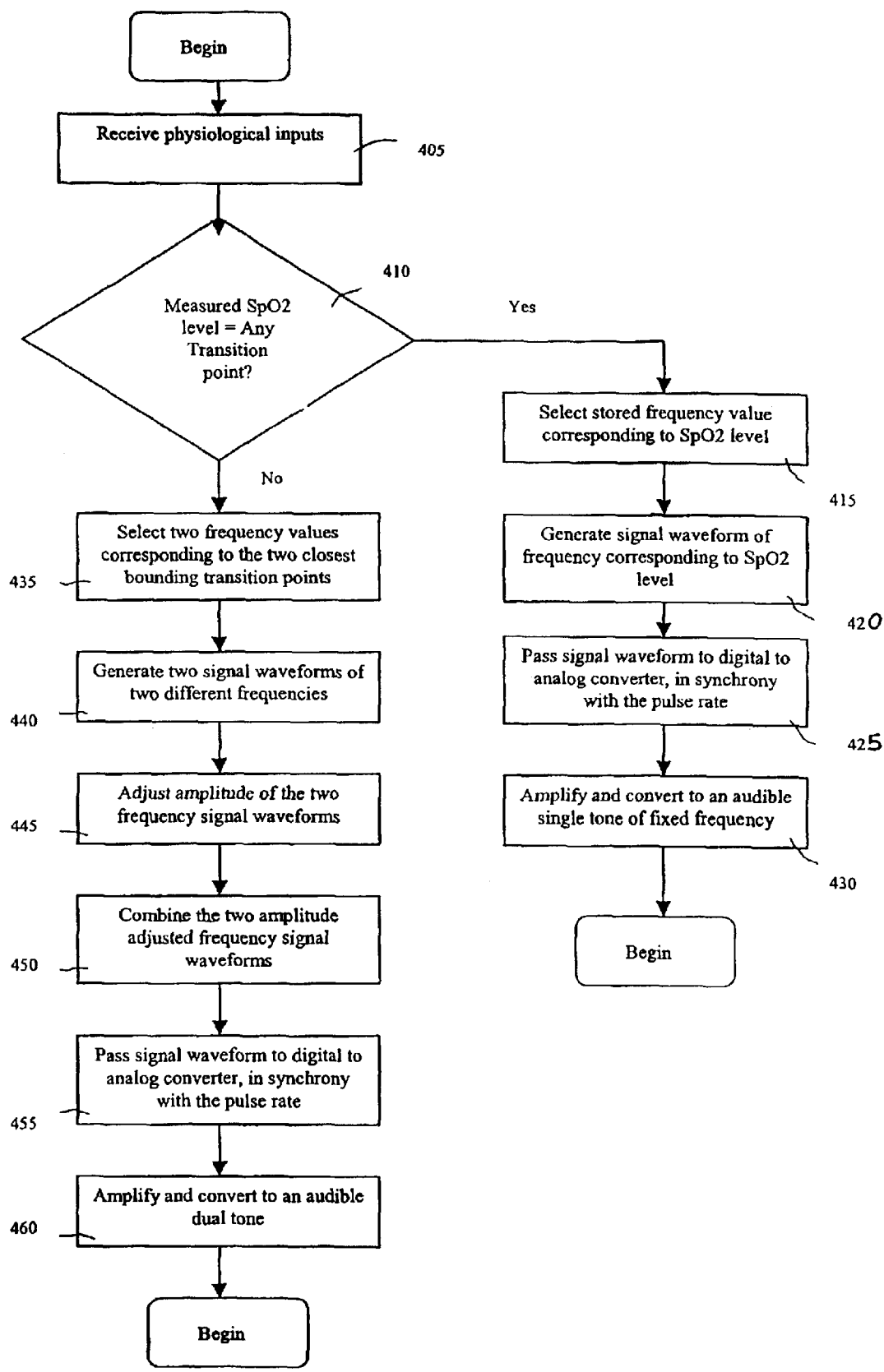
FIG. 4 is a flow diagram depicting a plurality of steps for generating audio indications for measured $SpO_2$ levels.

Referring now to FIG. 4, a flow diagram is shown depicting a plurality of steps of a preferred method of generating audio indications for measured $SpO_2$ levels that either correspond to predetermined transition points or that lie between any two bounding transition points. During operation, the sonification module receives 405 the measured level of oxygen saturation along with other physiological inputs such as the pulse rate and/or the original digitized plethysmographic waveform signal. The tone generator control then compares 410 the measured $SpO_2$ level with a set of predetermined transition points stored in the memory module. If the measured $SpO_2$ level matches one of the stored transition points, the corresponding stored frequency value is selected 415. Based on the frequency value selected, the tone generator control divides the basic reference clock frequency to generate 420 signal waveforms of frequency corresponding to the measured $SpO_2$ level. The frequency signals generated in step 420 are then passed 425 on to the digital to analog converter, in synchrony with the input pulse rate, and thereafter amplified and converted 430 to acoustic energy by a suitable audio outputting device such as a speaker.

However, if the measured $SpO_2$ level does not match with any of the stored transition points, the tone generator control selects 435 two frequency values $f_{x1}$ and $f_{x2}$ corresponding to the two closest transition points bounding the intermediate $SpO_2$ level. Referring back to FIG. 3, if the measured $SpO_2$ level is, for example, 98% then the two closest bounding transition points occur at the levels of 100% and 97% respectively. Therefore, the tone generator control generates 440 two signals of 661 Hz and 645 Hz that are the frequency values, $f_{x1}$ and $f_{x2}$, corresponding to the two closest transition points bounding the measured $SpO_2$ level of 98%.

The two frequency signals, $f_{x1}$ and $f_{x2}$, are next adjusted 445 in amplitude, through the amplitude control, by factors of $z_1$ and $z_2$, to generate modified signals $f_{x1}'$ and $f_{x2}'$ respectively. In a preferred embodiment, the factors $z_1$ and $z_2$ are chosen such that the sum of the two factors is 1. Also it is preferred that the individual values $z_1$ and $z_2$ be such that, out of the two frequency signals $f_{x1}$ and $f_{x2}$, they emphasize the amplitude of the frequency signal closer to the intermediate $SpO_2$ level, more, in comparison to the amplitude of the frequency signal that is farther away from the intermediate $SpO_2$ level. Such suitable values for the factors $z_1$ and $z_2$ are stored in the memory module.

Referring back again to FIG. 3, for an $SpO_2$ level of 98% the amplitude of the 661 Hz signal is adjusted by a factor of ⅓ while the amplitude of the 645 Hz signal is adjusted by a factor of ⅔. This is due to the fact that, out of the two closest bounding transition points, the $SpO_2$ level of 98% is closer to the transition point of 97% in comparison to the 100% transition point. Therefore, the amplitude of the frequency signal corresponding to the 97% transition point is emphasized more. Although the above described method of amplitude adjustment is preferred, it should be evident to persons of ordinary skill in the art that the factors $z_1$ and $z_2$ can take any suitable value that may either intensify or attenuate the amplitudes of the two frequency signals. Also, in alternate embodiments, the sum of the two factors $z_1$ and $z_2$ may be greater than or equal to 1. Finally, the two amplitude-adjusted frequency signals, $f_{x1}'$ and $f_{x2}'$, are combined 450 to generate a dual tone signal. The combined dual tone signal when passed 455 to the analog to digital converter, in synchrony with the input pulse rate, is transformed 460 by a speaker into an audible dual tone sound.

Referring back to FIG. 2, the output signal waveform, from the PSG 215, may be further shaped to resemble a desired form such as that of an exponentially decaying saw-tooth wave or any other shape known in the art. In a preferred embodiment, the single fixed frequency tones and/or the combined amplitude-adjusted dual tones are further shaped, by mixing them with the original digitized plethysmographic signals 240 so that, frequency and/or amplitude changes of the audio indications can be controlled by the detected waveform shape. Also, the user is able to not only associate the audible indication with changes in the measured levels of $SpO_2$ but also is able to hear the systolic and diastolic shape that is typical of oximetry signals.

Other embodiments and modifications of the present invention will occur readily to those of ordinary skill in the art in view of these teachings. For example, additionally or alternatively, it may be further desirable that the audio indications generated by the PSG be a pleasant tone, such as a bell type sound, comprising of a plurality of frequency content. The pleasant tone is a digitally recorded waveform, such as a wav file or mp3 file. As known to persons of ordinary skill in the art, this can be achieved by mixing a plurality of frequency signals, such as three significant frequency signals of a typical bell, and producing lower or higher pitch versions of the same depending upon the detected SpO2. This allows for a more pleasant sound to be heard instead of a simple tone.

Also, a user can dynamically control the range of $SpO_2$ measurements, the transition points, the corresponding frequency values and the amplitude modification factors $z_1$ and $z_2$ respectively, by modifying the respective control parameters stored in the memory module.

The present invention provides methods and devices for monitoring physiological data such that a health care provider is able to effectively monitor a patient's health status, including, for example, blood flow characteristics, without having to maintain constant visual contact. Since modifications can be made in the disclosed embodiments without departing from the scope of the invention, it is intended that the matter described so far be interpreted as illustrative rather than restrictive.

I claim:

1. A physiological data monitoring system for measuring at least one physiological characteristic, comprising:
   a sensor unit; and
   a monitoring unit in data communication with the sensor unit having a sonification module, said sonification module comprising at least one programmable sound generator module to produce a plurality of signals indicative of a physiological parameter and said sonification module being capable of storing a plurality of control parameters for managing the at least one programmable sound generator module wherein the signals produced have a plurality of frequencies, amplitudes, or frequencies in combination with amplitudes modified in accordance with at least one physiological data value, wherein the sonification module generates frequency tones, at a plurality of predetermined transition points, corresponding to a measured physiological parameter and wherein the transition points represent an appreciable change in the measured physiological parameter.

2. The physiological data monitoring system of claim 1 wherein the appreciable change has a value that is programmable by a user.

3. A pulse oximeter monitoring unit for measuring at least one blood flow characteristic through the application of at least one sensor having a plurality of light sources and at least one photodetector, comprising:
   a processor in data communication with the sensor wherein the processor transmits control signals to the light sources;
   a data acquisition module in data communication with said processor and said sensor unit wherein the data acquisition module receives input signals from the photodetectors;
   a memory module in data communication with said data acquisition module; and
   a sonification module in data communication with the memory module wherein the sonification module generates tones, at a plurality of predetermined transition points, corresponding to a measured $SpO_2$ level, wherein the transition points represent an appreciable change in the measured SpO2 level.

4. The pulse oximeter monitoring unit of claim 3 wherein the appreciable change has a value that is programmable by a user.

5. The pulse oximeter monitoring unit of claim 3 wherein the appreciable change is in the range of 2% to 5%.

6. A method of monitoring a patient's physiological status using a monitoring system that measures at least one physiological characteristic, comprising the steps of:
   sensing a value for a physiological characteristic;
   transmitting the value to a sonification module;
   receiving in the sonification module the transmitted value;
   comparing the value to a plurality of predetermined transition points;
   if the value matches one of said transition points, selecting a corresponding stored frequency value;
   based on the frequency value selected, generating signal waveforms having a frequency corresponding to the stored frequency value;
   transmitting the waveforms to a digital to analog converter;
   amplifying the converted waveforms;
   if the value does not match one of said transition points, identifying at least two transition points that approximate the value;
   selecting at least two frequency values corresponding to the at least two transition points;
   based on the at least two frequency values, generating at least two signal waveforms having frequencies corresponding to the at least two transition points;
   modifying amplitudes of the at least two signal waveforms; and
   mixing the at least two amplitude adjusted signal waveforms.

7. The method of claim 6 further comprising the step of:
   shaping the signal waveforms by mixing the said signal waveforms with a plurality of additional signals.

8. The method of claim 7 wherein the plurality of additional signals comprise plethysmographic signals.

9. The method of claim 6 further comprising the step of:
   mixing the signal waveforms with a plurality of frequency signals to generate a digital waveform.

* * * * *